United States Patent [19]

Ruiz et al.

[11] Patent Number: 4,650,464
[45] Date of Patent: Mar. 17, 1987

[54] METHOD FOR MONITORING INFUSION OF INTRAVENOUS FLUID INTO A PATIENT

[75] Inventors: Ernest Ruiz, Richfield; Michael S. Wenman, Minneapolis, both of Minn.

[73] Assignee: Minneapolis Medical Research Foundation, Inc., Minneapolis, Minn.

[21] Appl. No.: 747,720

[22] Filed: Jun. 21, 1985

[51] Int. Cl.⁴ ............................................. A61M 31/00
[52] U.S. Cl. ............................... 604/49; 128/DIG. 13; 177/25; 177/50
[58] Field of Search ............... 128/DIG. 12, DIG. 13; 604/44, 50, 65, 67, 151, 153, 246; 177/185, 211

[56] References Cited

U.S. PATENT DOCUMENTS

| | | | |
|---|---|---|---|
| 2,597,831 | 5/1952 | Willis | 177/185 |
| 2,706,755 | 4/1955 | Krasno . | |
| 3,287,721 | 11/1966 | Baehr . | |
| 3,389,387 | 6/1968 | Hulse et al. . | |
| 3,425,415 | 2/1969 | Gordon et al. . | |
| 3,656,478 | 4/1972 | Swersey | 604/153 |
| 3,690,318 | 9/1972 | Gorsuch . | |
| 3,934,474 | 1/1976 | Whitinger . | |
| 3,999,542 | 12/1976 | Shaw | 128/DIG. 12 |
| 4,137,915 | 2/1979 | Kamen . | |
| 4,176,349 | 11/1979 | Fliegel . | |
| 4,198,626 | 4/1980 | Rauscher . | |
| 4,253,457 | 3/1981 | McDonald . | |
| 4,320,855 | 3/1982 | Ricciardi et al. | 177/185 |
| 4,321,461 | 3/1982 | Walter, Jr. et al. . | |
| 4,378,014 | 3/1983 | Elkow . | |
| 4,379,995 | 4/1983 | Cocks et al. | 171/185 |
| 4,383,252 | 5/1983 | Purcell et al. . | |
| 4,411,649 | 10/1983 | Kamen . | |
| 4,449,538 | 5/1984 | Corbitt et al. | 604/50 |
| 4,457,750 | 7/1984 | Hill | 604/65 |
| 4,458,539 | 7/1984 | Bilstad et al. | 177/211 |
| 4,466,500 | 8/1984 | Mosher et al. | 177/50 |
| 4,553,619 | 12/1985 | Fujinaga | 177/25 |

Primary Examiner—Kyle L. Howell
Assistant Examiner—David Shay
Attorney, Agent, or Firm—Dorsey & Whitney

[57] ABSTRACT

The infusion of intravenous fluid into a patient is indirectly measured by monitoring the decreasing weight of an intravenous fluid receptacle as fluid flows from the receptacle to the patient. The method hereof includes the steps of taking a plurality of samples of the weight of the receptacle, calculating the difference between succeeding weight samples, comparing the weight difference against predetermined quality control criteria, taking additional samples if the criteria are not met, and converting the weight loss difference into volume of fluid infused into a patient. The apparatus hereof includes a transducer for sensing the weight of the fluid containing receptacle, circuitry for converting the analog signal generated by the transducer into a digital electronic electrical signal, and a processor for calculating the volume infused into a patient as a function of the second weight of the receptacle.

23 Claims, 6 Drawing Figures

METHOD FOR MONITORING INFUSION OF INTRAVENOUS FLUID INTO A PATIENT

TECHNICAL FIELD

This invention relates to a method and apparatus for monitoring the infusion of intravenous fluid into a patient. In particular, it pertains to a method and apparatus for indirectly measuring the infusion of liquids into a patient by monitoring the decreasing weight of an intravenous fluid receptacle as fluid flows from the receptacle to the patient.

BACKGROUND ART

It is often necessary, in the administration of intravenous fluids to a patient, to know exactly how much fluid a particular patient has received over a given period of time. This is particularly true in emergency resuscitation of a patient having a large blood loss. The amount of fluid accepted by a patient can give important indications as to the extent and the nature of the injury to the patient. Moreover, knowledge of the amount of fluid intravenously accepted by a patient can have a direct bearing on the nature of the treatment administered to the patient.

Current methods for measuring flow of intravenous fluid into a patient are labor intensive, and fraught with error. In particular, intravenous fluid such as blood, plasma, and saline solution are contained in bags in carefully metered amounts, and hung from a fluid administering support structure. The monitoring of the fluid infused in the patient is accomplished through visual observation and manual calculation by a nurse or other qualified person. The liquid volume of the bags is monitored visually as the liquid is infused into the patient. When one of the bags is emptied, it is removed and another is hung on the support structure to replace it. The replacement of bags, and the volume of each of the bags that are removed or added, are recorded on a "nursing sheet". From this sheet, the volume of flow over a particular period of time is calculated. As will be appreciated, this procedure can be very cumbersome, especially in emergency situations.

SUMMARY OF THE INVENTION

The problems outlined above are in large measure solved by the method and apparatus of monitoring infusion of intravenous fluid into a patient in accordance with the present invention. Specifically, the present invention provides for automatic monitoring of the amount of fluid infused into a patient without the need for visual inspection or manual calculations.

The method of measuring fluid flow into a patient in accordance with the present invention broadly includes the steps of taking a plurality of samples of the weight of the receptacle, calculating the difference between succeeding weight samples, comparing the calculated weight difference against a predetermined quality control criteria to ensure against invalid samples due to changing of bags, or the like, taking additional samples if the criteria are not met, and converting the weight loss into volume of fluid infused into a patient.

The apparatus for practicing the method in accordance with the present invention broadly includes a transducer for measuring the weight loss of a fluid receptacle as fluid flows from the receptacle into a patient and converting the weight of the receptacle into an analog electrical signal, an amplifier for increasing the power of the electrical signal, an analog to digital converter, and a processor for manipulating the digital data received from the analog digital converter.

DETAILED DESCRIPTION OF THE DRAWINGS

Figure 1:
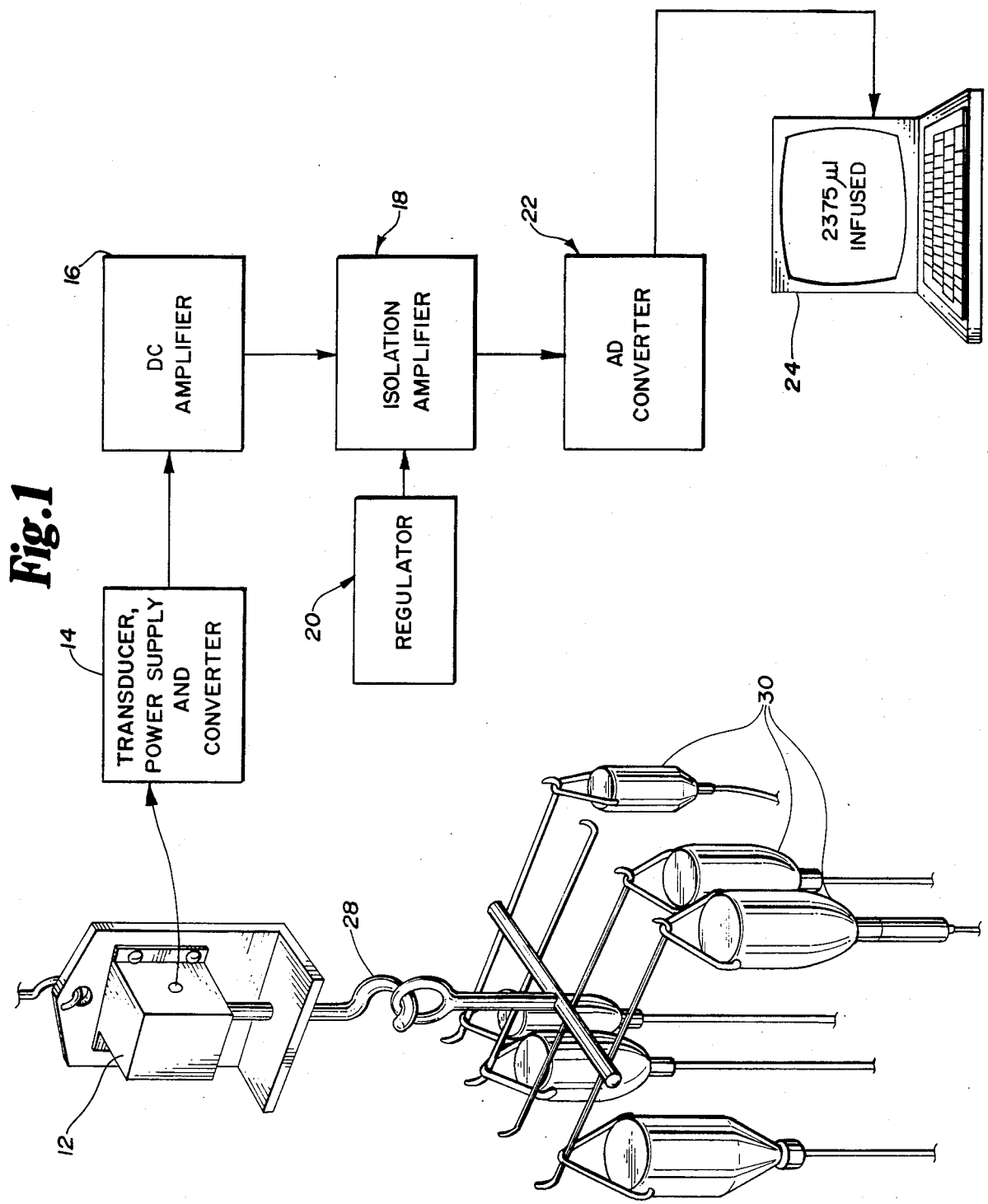
FIG. 1 is a block diagram of an apparatus for monitoring infusion of intravenous fluid into a patient in accordance with the present invention.

Referring to the drawings, an apparatus 10 for monitoring infusion of intravenous fluid into a patient in accordance with the present invention broadly includes a weight sensing transducer 12, a transducer power supply 14, a direct current amplifier 16, an isolation and ground referencing amplifier 18 including an adjustable regulator 20, an analog to digital converter 22, and a computer and display terminal 24. A rack 26 is suspended from weight transducer 12 by hook 28. A plurality of fluid containing bags 30 are carried by rack 26.

The weight sensing transducer 12 generates an analog signal corresponding to the weight of the rack 26 and fluid bags 30. The signal is transmitted, via intervening circuitry, to the analog to digital converter 22. The analog to digital converter 22 provides a digital signal, to computer 24, that corresponds to the weight suspended from hook 28 of transducer 12. The circuitry of apparatus 10 will be described in greater detail, with reference to FIG. 2, after the below detailed description of the flow charts depicted in FIGS. 3 and 4.

The weight indicating data received by computer 24 will decrease, at an approximately linear rate, as liquid is dispensed from bags 30 and is infused into a patient. The decreasing weight information can be readily converted into the amount of fluid infused into a patient. The weight data will also change (increase) as new bags are placed on rack 26, and will change (increase or decrease) when rack 26 is jarred. The volume of fluid infused into a patient is determined in accordance with the present invention by disregarding large changes in weight (due to addition of fluid bags to rack 26 or due to jarring of rack 26), and calculating the fluid infused only from weight data that decreases in approximately linear fashion.

Figure 3:
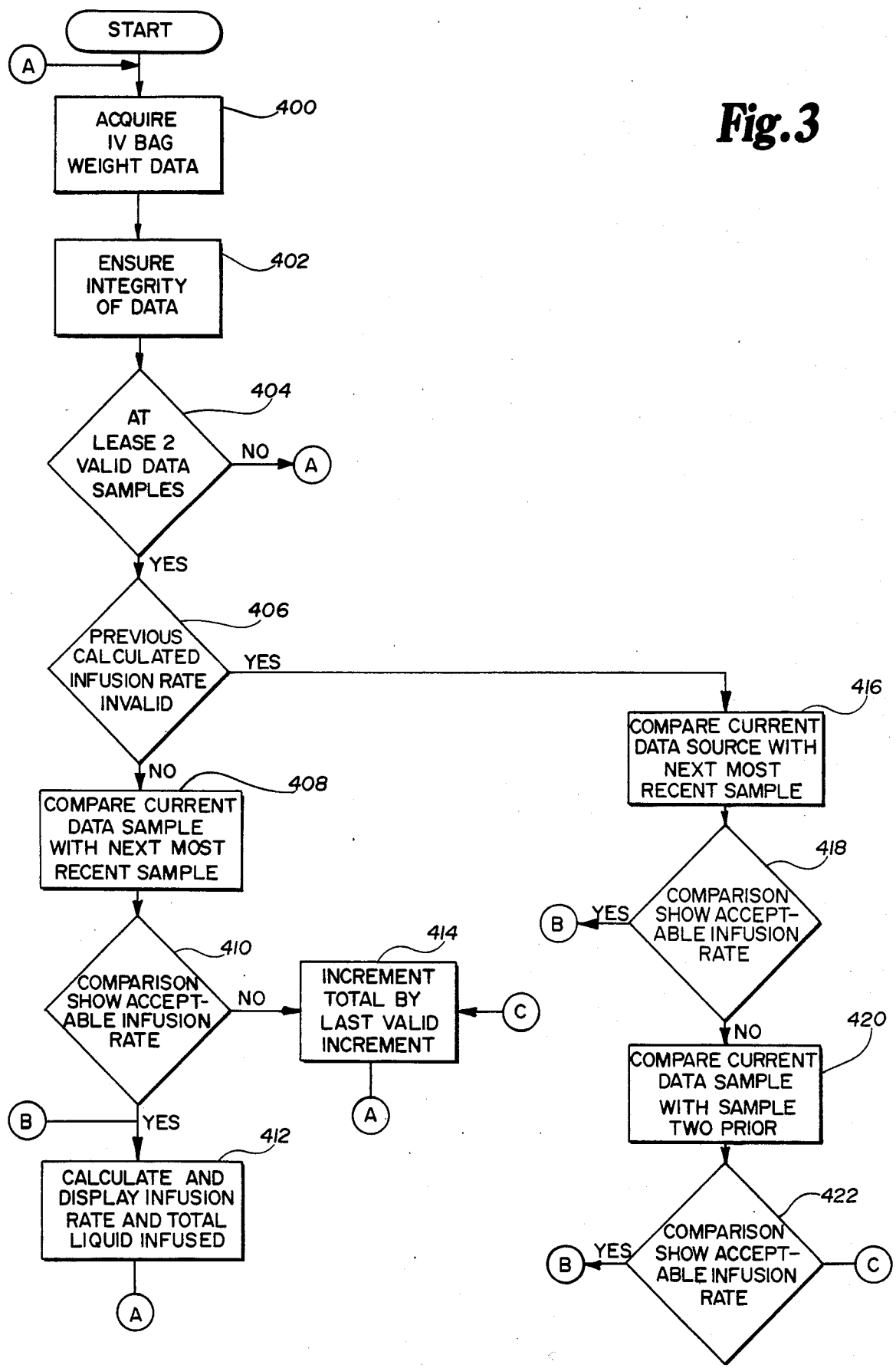
FIG. 3 is a schematic flow chart depicting the data processing methodology for monitoring the infusion of intravenous liquid into a patient in accordance with the present invention.

The basic steps for determining the amount of fluid infused into a patient in accordance with the present invention can be understood with reference to FIG. 3. Weight data must first be acquired from the transducer 12 and entered into the computer terminal 24 in digital format, as shown in functional block 400. The data is preferably acquired as a set of multiple readings. The multiple readings are averaged in block 402, and each reading is compared against the average to ensure the validity of each reading used to make up an individual sample. If at least two valid data samples have been acquired, block 404, an inquiry will be made as to whether the last calculation of infusion rate fell within acceptable limits, block 406.

The overall program flow will branch to functional block 408 to compute the fluid infusion rate, if the previous calculation of infusion rate was acceptable. Infusion rate is calculated at functional block 408 by comparing the most recent data sample with the next most recent sample, and dividing by the time elapsed between taking of the two samples. The calculated infusion rate is next compared to predetermined upper and lower limits, functional block 410. If the newly calculated infusion rate is acceptable, program flow will branch to functional block 412 to calculate the total amount of liquid infused into a patient, and to display the infusion rate and total liquid infused.

The infusion rate calculated at functional block 410 will fall within the predetermined acceptance levels only if the infusion rate shows a steady decline of liquid within bags 30. For instance, addition of a new bag to the rack 26 will show a sharp jump in weight, when the data sample taken immediately after a new bag 30 is added to rack 26 is compared to the next most recent data sample. Alternatively, the infusion rate will be outside of accepted limits if the rack 26 is jarred or otherwise moved at the time the weight data is being acquired. In either event, the overall program flow will be directed to functional block 414 if the infusion rate falls outside of accepted limits.

Functional block 414 estimates the total amount of fluid infused to a patient based on the last valid data sample, and the last computed valid infusion rate. Program flow is then directed to functional block 400 to acquire a new sample of a plurality of weight readings.

The program flow is directed to functional block 416 if the infusion rate calculated from the next most recent data sample fell outside of acceptable limits. Functional block 416 computes the infusion rate based on the most recent data sample and the next most recent data sample in the same manner as is done in functional block 408. The result of the comparison made in functional block 416 is compared against predetermined upper and lower limits in functional block 418. If the comparison shows an acceptable infusion rate, the program flow is directed to functional block 412 for calculation and display of the infusion rate and total liquid infused into a patient. The program flow will be transmitted from block 406 to 412, through functional blocks 416 and 418, if the next most recent data sample showed a large jump in weight, due to the addition of a new bag 30 the rack 26, and the most recent data sample shows an acceptable decrease in weight of the new bag.

The comparison of the most recent data sample to the next most recent data sample done in functional block 416 will be outside of acceptable limits if the next most recent data sample was invalid due to jarring of the rack 26. The jarring of the rack 26 would produce a large shift in weight data (either increase or decrease) that would hopefully have settled out by the time the most recent data sample was taken. For that reason, if the comparison of the most recent data sample to the next most recent data sample is determined not to be within acceptable limits in block 418, the program will branch to functional block 420 where the most recent data sample will be compared to two samples prior. As will be appreciated, comparison of the most recent data sample to the data sample two prior will disregard the intermediate, next most recent data sample, when calculating infusion rate. The comparison made in functional block 420 is evaluated against acceptable upper and lower limits in functional block 422. If the comparison is within acceptable criteria, the program will branch to the previously described functional block 412. If the comparison is not within the allowed criteria, the program will branch to previously described block 414.

Figure 4A:
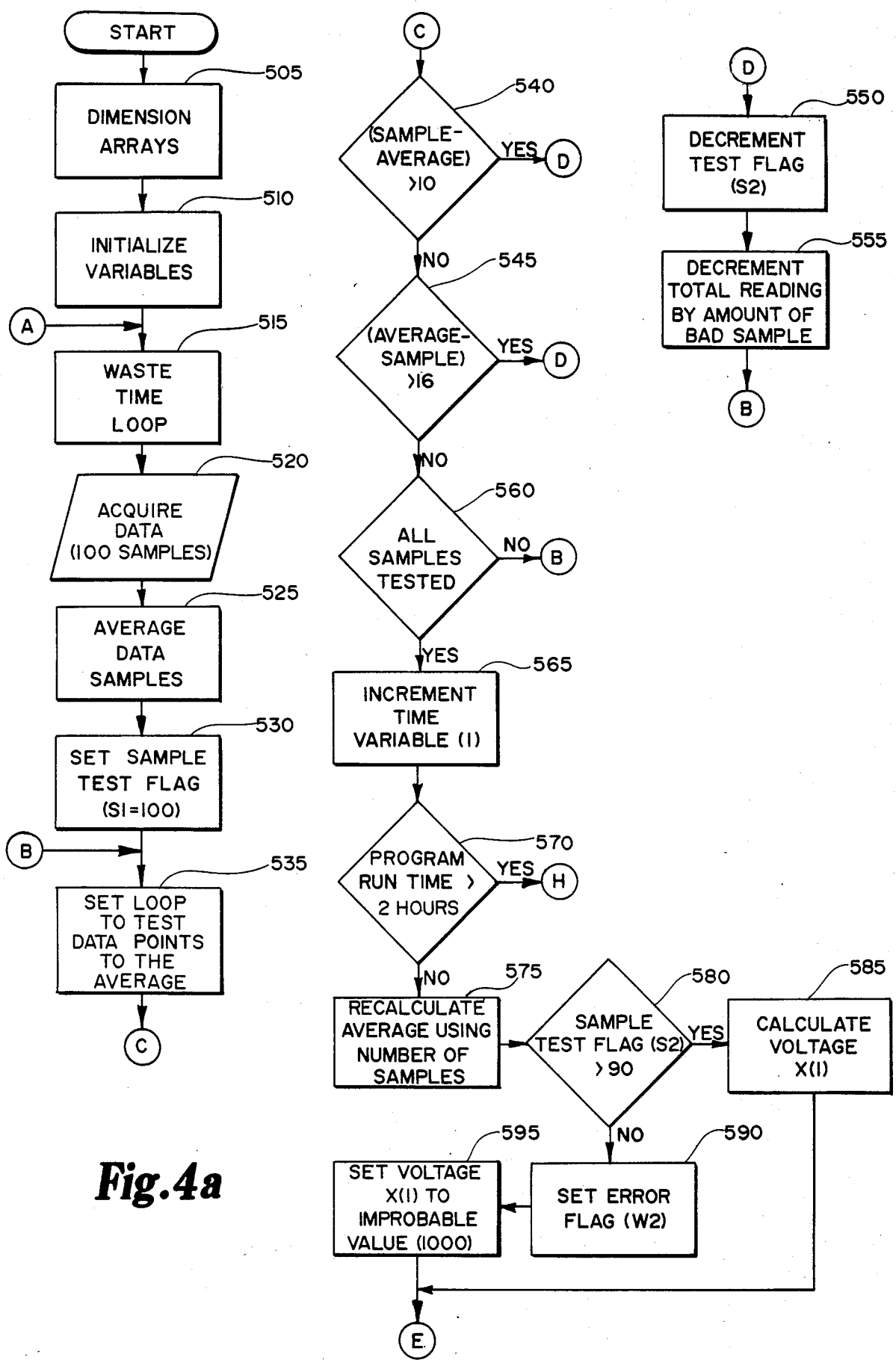
FIGS. 4a, 4b, and 4c are interrelated portions of a detailed flow chart for implementing the methodology depicted in FIG. 3.
Figure 4B:
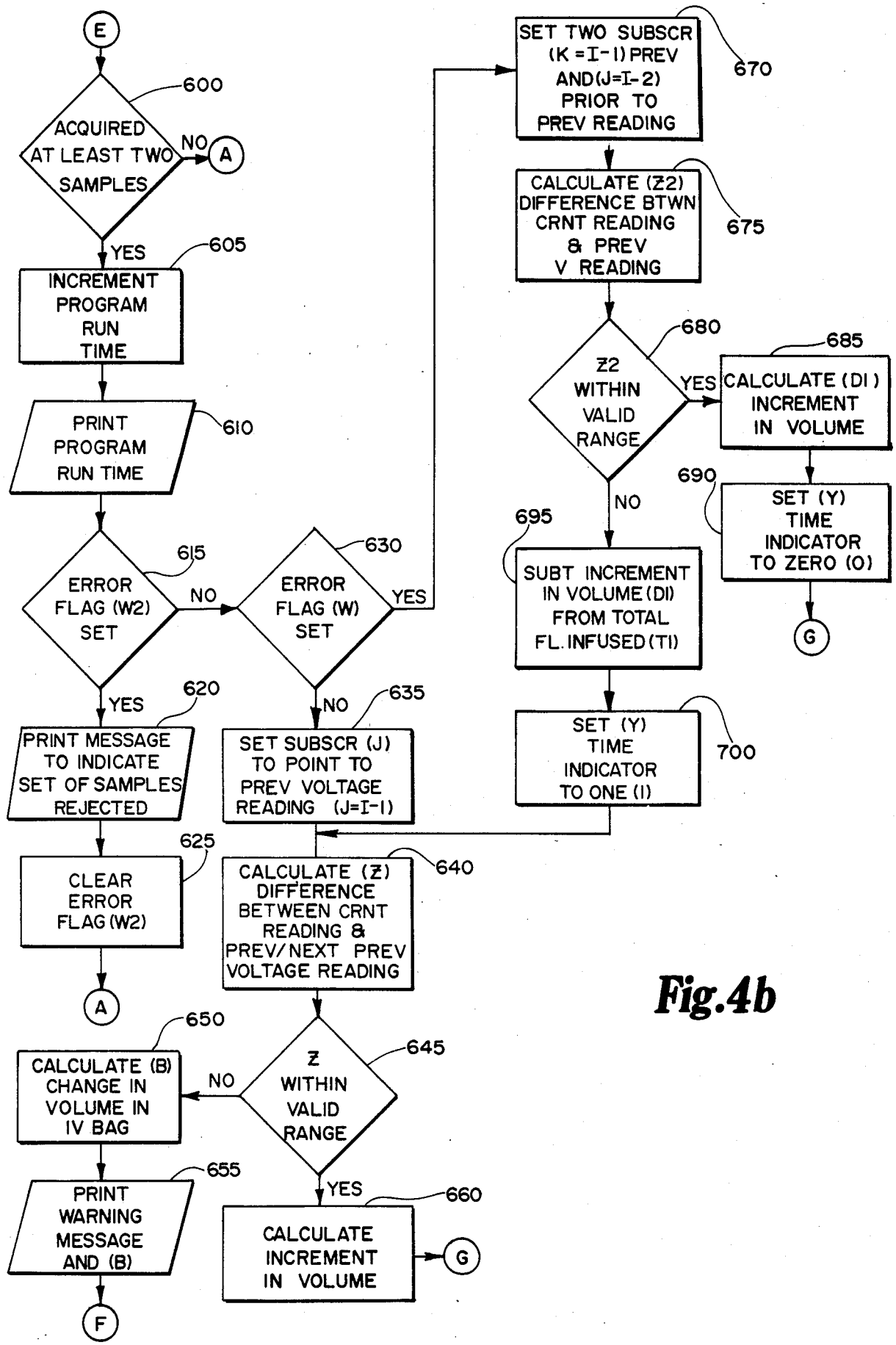
Figure 4C:
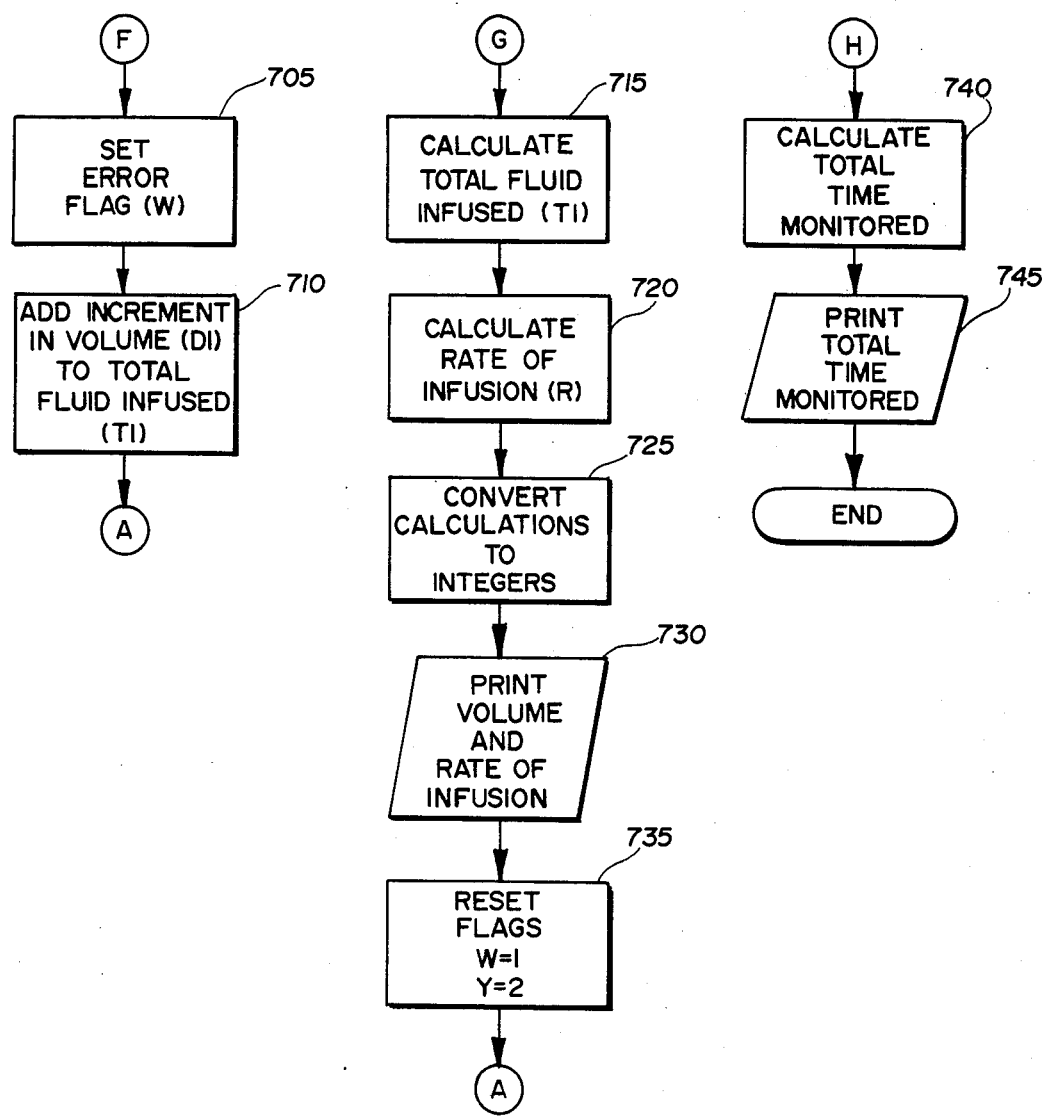

FIGS. 4a, 4b, and 4c comprise a detailed flow chart of the software used to calculate the rate of infusion of intravenous fluids and the total volume of intravenous fluid infused into a patient over a two hour period. A program listing, written in BASIC, for executing the software on a PET Commodore Business Machine, is included at the end of this specification.

Function 505 sets up three arrays which are used to accumulate data output from the A/D converter 22. The first array is set up to acquire 100 data readings for each data sample. The program is designed to take 100 data readings to make up one data sample every 30 seconds. A second array, dimensioned V(240), is used to acquire and store the data samples taken from each set of 100 data samples over a two hour period. The third array, dimensioned X(240), is used in conjunction with array V to provide increasing numerical readings, corresponding to decreasing weight data samples, to indicate an increasing volume of fluid infused into a patient, as the weight of the bags 30 decreases. Function 510 is used to initialize variables and constants used throughout processing, as indicated in lines 60 to 140 of the program listing.

It takes a short period of time to acquire 100 data readings. A "waste time" loop, function 515, is therefore added prior to the data acquisition function 520 to bring the total elapsed time between taking of data samples to 30 seconds. The 30 second time interval is used in several places in the program. First, successive intervals are cumulatively added to determine elapsed time into the program, function 605, and to print the elapsed time, function 610. The 30 second interval is also used to limit program run time to a two hour period, functions 565 and 570. At two hours run time, the program will branch to function 740, which calculates total run time, and then to function 745 which prints total run time on the screen. The program then terminates.

The next part of the program is designed to eliminate invalid data readings that may have been acquired in function 520. Function 525 averages the data readings and stores the average reading. Function 530 sets up a sample test flag which is used to determine that at least 90 data samples are within an acceptable variance of the average calculated in function 525. Function 535 sets up a loop to test all 100 data points acquired and totaled in function 520. Each sample is tested to determine whether it is more than 4.1% greater (function 540) or 6.7% less than the average. The 4.1% and 6.7% values are preferred limits; the limits may vary between 25% greater and 25% less than the average. If the variance is outside the above mentioned criteria, then the data reading is disregarded and processing is directed to functions 550 and 555. Function 550 decrements the test flag set up in function 530 and function 555 decrements the total cumulative reading accumulated in function 520 by the amount of the bad sample.

Function 560 tests to see if all 100 data readings have been tested for validity. Function 565 increments the time variable and function 570 tests the time variable to see if it exceeds two hours. If program time does not exceed the two hour maximum, function 575 recalculates the average of the 100 data readings just acquired, using the number of valid data readings that passed through the tests in functions 540 and 545, and the total cumulative reading as amended by function 555.

Function 580 tests for the number of valid data readings. The entire batch of 100 data readings will be rejected, and an error flag will be set in function 590, if the number of valid sample data points is 90 or less. Function 595 sets the data sample to an improbable value which will be printed on the screen of terminal 24 as a warning device by function 620. Processing is directed to function 585 if the number of valid sample data points is greater than 90, where the numerical volume of the data sample is subtracted from a predetermined maximum. The substraction step is included so that an increasing value (representing increase of fluid infused into a patient) is generated from the decreasing value (decrease of weight) measured by transducer 12.

Processing is next directed to function 600 where the program determines whether or not at least two batches (samples) of data readings have been acquired. Assuming at least two samples exist, processing is directed to functions 605 and 610, both previously described.

The program next proceeds to function 615, where the status of the flag set by function 590 is checked to determine whether the most recent data sample is based on more than 90 data readings. The program is branched to function 620, where a warning message is printed on the screen of terminal 24, if the data sample is based on 90 or less weight readings. The flag set at function 590 is then cleared at function 625, and the program proceeds to function 515 to acquire another set of 100 readings.

The program next calculates infusion rate from the data samples accepted in the first part of the program. The first step in this portion of the program is to determine whether or not the last calculation of infusion rate made by the program fell within acceptable limits. The determination is made at function 630 by testing the status of a flag set by function 705. Processing is directed to function 635, if the last calculation was valid, where the subscript for the minuend of the difference calculation performed in function 640 is set to point to the previous data sample. Processing then moves to function 640 where the difference between the current sample and the next most recent sample is calculated. The difference is then tested to be within the valid range, function 645. The acceptable range as defined in the program is from zero to $M = 470$ cc. A difference of less than zero would indicate a negative flow of fluids (i.e., more fluid in the bag than the previous reading). A difference greater than 470 cc indicates a flow of fluid that is too rapid (i.e., a flow rate of 940 cc/min, which is a faster flow rate than is possible with intravenous infusion).

Processing is directed to function 650 and 655 if the difference in succeeding data samples is outside the acceptable range. Function 650 calculates the (erroneous) change in volume in the IV bags, and function 655 prints the erroneous amount as a warning message on the screen. Function 705 then sets the error flag (w), to be tested at function 630 during processing of the next data sample and directs processing to function 710. Function 710 adds an estimated increment to the value representing total volume of fluid. The estimated value is based on the volume change during the previous interval. Processing is next directed to function 515 to acquire a new batch of sample readings over a 30 second period.

The difference calculated in function 640 is accepted for calculating the rate of infusion and the total volume infused, if the difference is within the criteria established at function 645. Processing is directed to function 660 where the actual increment in volume of fluid infused is calculated, based on the actual difference in weight of the current sample and the next most recent sample. The total fluid infused is next calculated at function 715 by adding the increment calculated in function 660 to the cumulative total. The rate of infusion is then calculated at function 720. Function 725 converts the calculations to integers, and function 730 prints the volume of intravenous fluids infused and the rate of infusion on the display of monitor 24. Function 735 resets flags to their initial value, and processing is directed back to function 515 to acquire an additional batch of data samples over the next 30 second period.

As described above, an error flag is set by function 705 if the difference in succeeding readings is determined to be outside the valid range at module 645. Setting of the flag will direct the program flow to function 670, when the next data sample is processed through the program. Function 670 sets two subscripts. One subscript is used to reference the next most recent data sample, and a second subscript is used to reference the data sample immediately prior to the next most recent data sample. Function 675 checks the difference between the current data sample and the next most recent data sample. Function 680 tests the difference determined in function 675 for validity in the same manner as described for function 645 above. Processing is directed to function 685 if the difference is determined to be valid, and the increment in volume is calculated at function 685 in the same manner as in function 660. The timer indicator is set at function 690 for calculation of infusion rate based on a 30 second time interval (the time between succeeding data samples). The program flow is directed to function 715 from function 690. Function 715 calculates the total fluid infused based on the actual increment calculated at function 685.

Program flow is directed to function 695 if the difference between the current data sample and next most recent data sample, as calculated in function 675, is outside the established criteria. At function 695, the (invalid) increment that was calculated in the previous pass, and added to the overall fluid infused value at function 710, is subtracted from the total fluid infused value. The timer indicator is reset at function 700 for calculation of infusion rate based on a 60 second time interval (the time between the first and third of three data samples).

Processing is next directed to function 640 for calculating the difference between data samples. The subscript for the minuend used in the difference calculation was set, by function 670, to point to the data sample prior to the next most recent data sample; i.e., to the data sample two prior to the current sample. Processing is next directed to function 645, and continues as previously described.

Figure 2:
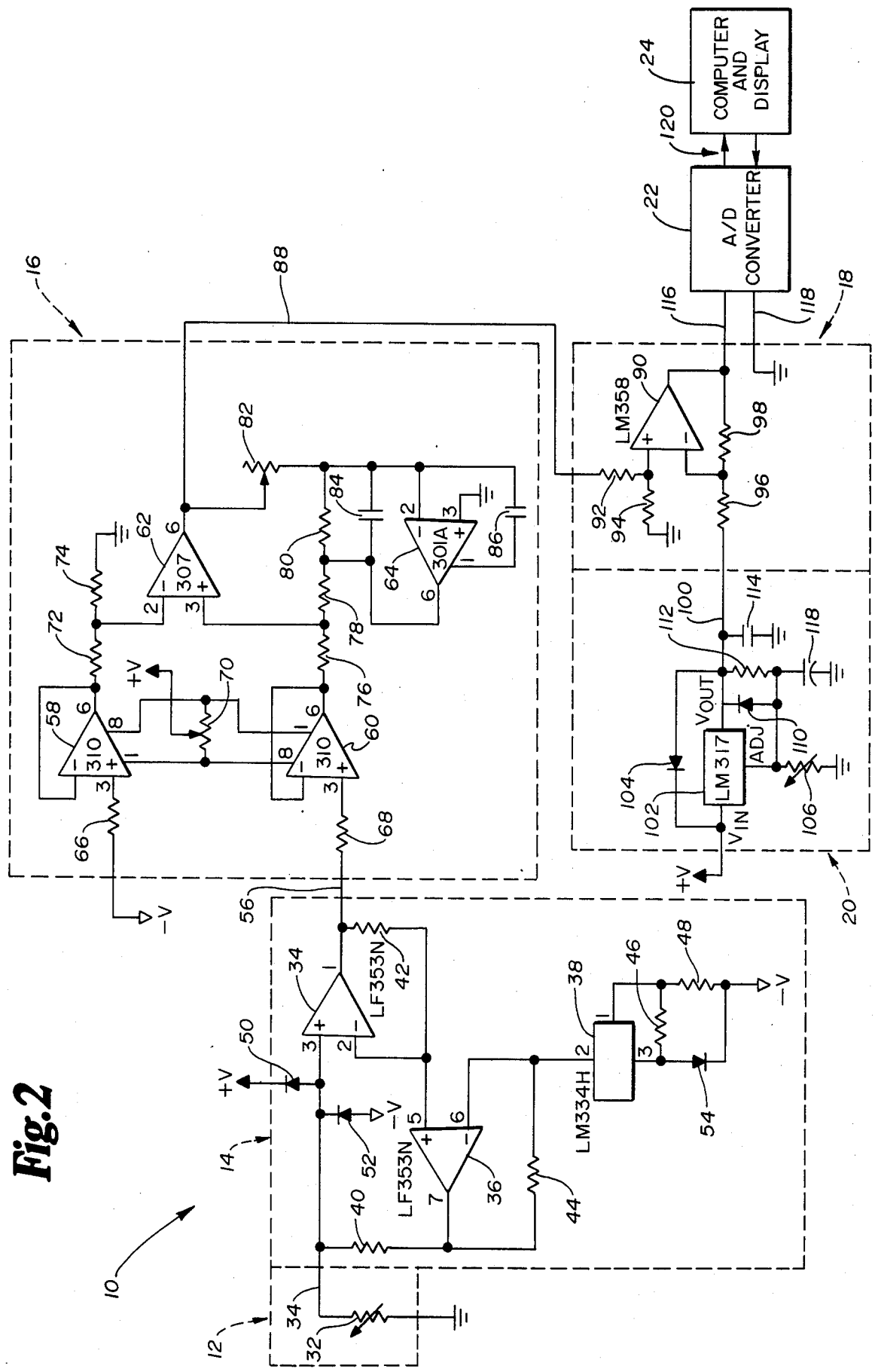
FIG. 2 is an electrical schematic diagram of the present invention.

Referring to FIG. 2, the circuitry of the apparatus 10 in accordance with the present invention will be described in detail.

Weight sensing transducer 12 advantageously comprises a uniMeasure/80 weight testing transducer manufactured by the Unimeasure Company of 909 Williamson Loop, Grants Pass, Oreg. 97526. The weight transducer 12 comprises a variable resistor that varies in resistance from 150 to 300 ohms. The weight transducer 12 is electrically connected to power supply 14 via lead 34.

Power supply 14 comprises a constant current supply source for the variable resistance 32. The power supply comprises two halves 34, 36 of an LF353N wide bandwidth dual JFET input op-amp semiconductor chip manufactured by National Semiconductor Corporation of 2900 Semiconductor Drive, Santa Clara, Calif. 95051, and an LM334H 3-terminal adjustable current source semiconductor chip 38 also manufactured by National Semiconductor Corporation. Various feedback and biasing resistors 40, 42, 44, 46, 48, with values as indicated in FIG. 2, are connected to the indicated pin numbers of the chip numbers 34, 36, 38. Power supply 14 includes diodes 50, 52, 54; diode 50 being connected to a +12 volt DC power source, and diodes 52, 54 being connected to a −12 volt DC power sources.

Power supply 14 is connected to DC amplifier 16 via lead 56. DC amplifier 16 includes two LM310 Voltage Follower semiconductor chips 58, 60 a single op-amp LM307 semiconductor chip 62 and a single LM301A op-amp semiconductor chip 64 all manufactured by the National Semiconductor Corporation. Resistors 66, 68, 70, 72, 74, 76, 78, 80 and 82 are connected to respective chip pins as indicated in the drawing. Capacitors 84, 86 are connected to respective pins of the 301A semiconductor chip 64, as depicted in FIG. 2. The resistors and capacitors referred to above have the values shown in the drawing. A minus 12 volt DC source is connected to pin 3 of the 310 chip 58 via resistor 66. Positive 18 volts DC is provided to the variable 1K ohm resistor 70 as an offset adjustment. A 10K ohm resistor 74, and pin 3 of the 301A chip 64 are connected to ground. Power supply 16 is connected to ground referencing amplifier 18 via lead 88.

Ground referencing amplifier 88 comprises one-half of an LM358 low power dual op-amp semiconductor chip manufactured by National Semiconductor Corporation. The amplifier 18 includes input resistors 92, 94, 96, and feedback resistor 98. Values of the resistors are as shown in FIG. 2. Adjustable regulator 20 is connected to the ground referencing amplifier 18 via lead 100.

Regulator 20 is based around a LM317 3-terminal adjustable voltage regulator semiconductor chip 102 manufactured by National Semiconductor Corporation. The "voltage in" terminal of the LM317 chip is connected to a +12 volt DC power source. The "voltage out" terminal of the LM317 chip is connected, via lead 100, to the ground referencing amplifier 18. The "voltage in" and "voltage out" terminals are interconnected by diode 104. The "adjustment" terminal is connected to ground via convertible resistor 106 and capacitor 108. Diode 110 and resistor 112 are connected between the adjustment and voltage in terminals of the LN317 chip. The voltage out terminal is connected to ground via capacitor 114.

Ground referencing amplifier 18 is connected to the analog to digital converter 22 via lines 116, 118. The analog to digital converter advantageously comprises an AIM 16 analog input module manufactured by Connecticut microComputer, Inc. of 34 Delmar Drive, Brookfield, Conn. 06804. The AIM 16 analog input module is a 16 channel analog to digital converter. An analog signal input to the AIM 16 module is converted to an 8 byte digital signal. The analog to digital converter 22 is connected to the computer and display 24 via data bus 120.

```
READY.

5 DIM X(240)
10 DIM D9(100)
20 DIM D(16)
40 DIM V(240)
50 OPEN 4,4
60 T1=0
70 Y=0
80 I=0
90 H=0.5
100 W=1
110 W2=0
120 S=29.38
140 M=16.02
147 PRINT"THE RUN STOP KEY MAY BE USED TO"
148 PRINT"STOP MONITORING AT ANY TIME."
149 Q=119.5
150 PRINT
180 FOR H=1TO20700:NEXT
200 IE=59426
210 UP=59471
220 K=129+64
230 POKE IE,K
240 D5=0
250 FOR P=1TO100
260 POKE IE,0
270 POKE IE,K
```

```
280 D(0)=PEEK(UP)
290 D9(P)=D(0)
300 D5=D5+D9(P)
310 NEXT P
311 A=D5/100
312 S1=100
313 FOR O=1TO100
314 IF(D9(O)-A)>10. THEN 317
315 IF(A-D9(O))>16. THEN 317
316 GO TO 319
317 S1=S1-1
318 D5=D5-D9(O)
319 NEXT O
320 PRINT
330 I=I+1
340 IF I>(Q*2) THEN 700
350 V(I)=D5/S1
351 IF S1>90 THEN 360
352 W2=1
353 X(I)=1000.
354 GO TO 380
360 X(I)=255-V(I)
380 IF I=1 THEN 180
390 N=N+.5
400 PRINT
410 PRINT
420 PRINT
430 PRINT N;"MINUTES INTO CASE."
435 PRINT#4,N;"MINUTES INTO CASE."
436 IF W2=0 THEN 440
437 PRINT "SAMPLING ARTIFACT."
438 W2=0
439 GO TO 180
440 IF W=0 THEN 470
450 J=I-1
460 GO TO 485
470 J=I-2
471 K=I-1
472 Z2=X(I)-X(K)
473 IF Z2<0 THEN 480
474 IF Z2>M THEN 480
475 D1=Z2*S
476 Y=0
477 GO TO 520
480 Y=1
482 T1=T1-D1
485 Z=X(I)-X(J)
490 IF Z<0 THEN 630
500 IF Z>M THEN 630
510 D1=Z*S
520 T1=T1+D1
530 R=(D1*2)/(Y+1)
540 TL=INT(T1)
550 R=INT(R)
560 PRINT
570 PRINT"PRESENT RATE OF INFUSION IS";R;"MLS./MIN."
575 PRINT#4,"PRESENT RATE OF INFUSION IS";R;"MLS./MIN."
```

```
580 PRINT
590 PRINT"TOTAL VOLUME INFUSED IS";TL;"MLS."
595 PRINT#4,"TOTAL VOLUME INFUSED IS";TL;"MLS."
600 W=1
610 Y=0
620 GO TO 190
630 B=INT(S*2)
640 PRINT
650 PRINT"CHECK IX SETUP, THE VOLUME"
660 PRINT"CHANGE IS";B;"MLS."
670 W=0
680 T1=T1+D1
690 GO TO 180
700 F=I/2
710 PRINT
720 PRINT
730 PRINT;F;"MINUTES OF MONITORING OMPLETED."
735 CLOSE4
740 END
READY.
```

We claim:

1. A method for monitoring the intravenous flow of fluid into a patient from a fluid containing receptacle, comprising the steps of:
   a. taking a set of time spaced weight data readings of the weight of the receptacle;
   b. repeating substep a if said set of time spaced weight data readings is the first such set taken;
   c. determining the difference in weight of said receptacle between the most recent set of time spaced data readings, and the immediately preceding set of said time space weight data readings;
   d. determining if the weight difference calculated in step c represents a predetermined acceptable weight decrease for said fluid receptacle;
   e. converting the weight difference calculated in step c to the value of the incremental volume of fluid transferred to said patient between the taking of the most recent set of weight data readings and the taking of the immediately preceding set of weight data readings, if said weight difference represents a predetermined acceptable change in the weight of the receptacle;
   f. repeating substeps a through d if the weight difference calculated in substep c was not acceptable and was the first such weight difference calculated;
   g. determining the weight difference of said receptacle between the most recent set of weight data readings and a set of weight data readings at least two prior to said most recent set of weight data readings if the weight difference calculated in substep c did not reflect an acceptable weight decrease for said fluid receptable;
   h. determining if the weight difference calculated in step g represents an acceptable weight decrease for said fluid receptacle;
   i. converting the weight difference calculated in step g to the value of the incremental volume of fluid transferred to said patient between the taking of the most recent set of weight data readings and the taking of the set of weight data readings at least two prior to the most recent set that was used to determine the weight difference in step g, if the weight difference determined in step g represents an acceptable weight decrease for said fluid receptacle;
   j. determining the total volume of fluid transferred to said patient by summing the respective incremental volumes determined in steps e and i;
   k. repeating steps a thru i until said total volume of fluid reaches a desired level.

2. The method as claimed in claim 1 wherein substep a comprises the further substep of determining the average value of said set of weight data readings.

3. The method as claimed in claim 2 wherein substeps c and g of claim 1 comprise the further substep of determining the weight difference of said receptacle between sets of weight data readings by comparing the average values of those sets of weight data readings.

4. The method as claimed in claim 1 wherein substeps d and h comprise the further substeps of comparing said weight difference to predetermined acceptable weight difference upper and lower limits to determine if said weight difference represents a predetermined acceptable weight decrease for said fluid receptacle.

5. The method as claimed in claim 4 wherein said predetermined acceptable weight difference lower limit is set not less than zero.

6. The method as claimed in claim 4 wherein said Predetermined acceptable weight difference upper limit is set at a value corresponding to the maximum rate at which said patient can receive intravenous infusion.

7. The method as claimed in claim 6 wherein said predetermined acceptable upper limit is set at a value corresponding to an intravenous fluid flow rate of 940 cc/min.

8. A method for monitoring the infusion of intravenous fluid into a patient from a fluid containing receptacle, comprising the steps of:
   a. taking a set of time spaced weight data readings of the weight of the receptacle;
   b. repeating substep a if said set of weight data readings is the first such set taken;
   c. determining if there has been a calculation of the receptacle weight difference between two or more sets of weight data readings;
   d. determining, if there has been a calculation of the receptacle weight difference between sets of weight data readings, if the last of said calculations of said receptacle weight difference was acceptable;

e. determining a receptacle weight difference from the most recent set of weight data readings and the set immediately preceding said most recent set of weight data readings;

f. determining whether the receptacle weight difference calculated in substep e is acceptable;

g. determining a receptacle weight difference from the most recent set of weight data readings and the set of weight data readings at least two sets prior to said most recent set of weight data readings if the receptacle weight difference calculated in substep e was not acceptable and there has been a previous calculation of the receptacle weight difference between sets of weight data readings and if the most recent of said previous calculations of the receptacle weight difference was not acceptable;

h. determining whether, if the receptacle weight difference was calculated in substep g, said weight difference is acceptable;

i. converting the weight difference calculated in substep e into the value of the volume of fluid represented by said weight difference if said weight difference is acceptable;

j. Converting the weight difference calculated in substep g into the value of the volume of fluid represented by said weight difference if the weight difference calculated in substep e was not acceptable and the weight difference calculated in substep g was acceptable;

k. adding said fluid volume value to the sum of all previous fluid volume values calculated if the weight difference calculated in substeps e or g was acceptable;

l. subtracting a value equal to the most recent of said fluid volume values added to said sum of fluid volume values from said sum of fluid volume values if the weight difference calculated in substep g was acceptable;

m. adding a fluid volume value to said sum of all previous fluid volume values that is equal to the next most previous fluid volume value that reflected an acceptable change in the weight of said fluid receptacle if the weight difference calculated in substeps e or g did not reflect an acceptable weight decrease for said fluid receptacle;

n. repeating substeps a through l if there has not been a previous calculation of the receptacle weight difference between sets of weight data readings that was acceptable;

o. repeating substeps a through m until said sum of fluid volume values reaches a desired level.

9. The method as claimed in claim 8, wherein substep a comprises the further substep of determining the average value of said set of weight data readings.

10. The method as claimed in claim 9, wherein substeps e and g of claim 19 comprise the further substep of determining said receptacle weight difference by comparing the average values of said sets of weight data readings.

11. The method as claimed in claim 9, wherein substep a comprises the further substep of comparing each of said weight data readings against predetermined upper and lower limits, and rejecting those weight data readings that are outside of said limits.

12. The method as claimed in claim 11 wherein substep a of claim 8 comprises the further substep of calculating the average value of said set of weight data readings using only those weight data readings that were within said predetermined upper and lower limits.

13. The method as claimed in claim 12 wherein substeps e and g of claim 8 comprise the further substep of determining said receptacle weight difference by comparing the average values of said sets of weight data readings.

14. The method as claimed in claim 11, wherein said upper limit is set at a value not more than 25% greater than said average value of said set of weight data readings.

15. The method as claimed in claim 11, wherein said lower limit is set as a value not less than 25% lower than said average value of said set of weight data readings.

16. The method as claimed in claim 11, wherein said upper limit is set at a value not more than 4.1% greater than said average value of said set of weight data readings.

17. The method as claimed in claim 11, wherein said lower limit is set at a value not less than 6.7% lower than said average value of said set of weight data readings.

18. The method as claimed in claim 11, including the step of rejecting said set of data readings when more than a predetermined number of said data readings are outside of said limits.

19. The method as claimed in claim 18, wherein said predetermined number of said data readings is set at 10% of the total number of said data readings within said set of data readings.

20. The method as claimed in claim 8, wherein substeps f and h comprise the further substeps of comparing said weight difference to predetermined acceptable upper and lower weight difference limits, and rejecting said weight difference if said weight difference falls outside said weight difference limits.

21. The method as claimed in claim 20, wherein said predetermined acceptable weight difference lower limit is set not less than zero.

22. The method as claimed in claim 20, wherein said predetermined acceptable weight difference upper limit is set at a value not more than the value corresponding to the maximum rate at which said patient can receive intravenous infusion.

23. The method as claimed in claim 22, wherein said predetermined acceptable weight difference upper limit is set at a value corresponding to an intravenous fluid flow rate of 940 cc/min.

* * * * *

UNITED STATES PATENT AND TRADEMARK OFFICE
CERTIFICATE OF CORRECTION

PATENT NO. : 4,650,464

DATED : March 17, 1987

INVENTOR(S) : Ernest Ruiz and Michael S. Wenman

It is certified that error appears in the above-identified patent and that said Letters Patent is hereby corrected as shown below:

In the abstract, last line, delete the word "second" and substitute therefor --sensed--.

Column 1, line 6, delete the words "and apparatus".

Column 1, line 47, delete the words "and apparatus".

Column 5, line 15, delete the word "substraction" and substitute therefor --subtraction--.

Column 8, line 23, delete the word "LN317" and substitute therefor --LM317--.

Column 12, line 51, delete the word "Predetermined" and substitute therefor --predetermined--.

UNITED STATES PATENT AND TRADEMARK OFFICE
CERTIFICATE OF CORRECTION

PATENT NO. : 4,650,464

DATED : March 17, 1987

INVENTOR(S) : Ernest Ruiz and Michael S. Wenman

It is certified that error appears in the above-identified patent and that said Letters Patent is hereby corrected as shown below:

Column 13, line 27, delete the word "Converting" and substitute therefor --converting--.

Column 14, line 23, delete the word "as" and substitute therefor --at--.

Signed and Sealed this

Twenty-ninth Day of September, 1987

Attest:

DONALD J. QUIGG

Attesting Officer    Commissioner of Patents and Trademarks